United States Patent
Fell

[11] Patent Number: 6,123,655
[45] Date of Patent: Sep. 26, 2000

[54] CELL SEPARATION SYSTEM WITH VARIABLE SIZE CHAMBER FOR THE PROCESSING OF BIOLOGICAL FLUIDS

[76] Inventor: Claude Fell, Route du Stand 22, CH-1260 Nyon, Switzerland

[21] Appl. No.: 09/147,117
[22] PCT Filed: Aug. 2, 1996
[86] PCT No.: PCT/IB96/00771
  § 371 Date: Oct. 9, 1998
  § 102(e) Date: Oct. 9, 1998
[87] PCT Pub. No.: WO97/15399
  PCT Pub. Date: May 1, 1997

[30] Foreign Application Priority Data

Apr. 24, 1996 [WO] WIPO ............... PCT/IB96/00373

[51] Int. Cl.$^7$ .................................................. B04B 1/02
[52] U.S. Cl. ........................................ 494/50; 494/67
[58] Field of Search ............................. 494/1, 10, 31, 494/36, 37, 38, 41, 43, 45, 47, 48, 50, 51, 56, 60, 63, 67, 84

[56] References Cited

U.S. PATENT DOCUMENTS

| | | |
|---|---|---|
| 2,661,150 | 12/1953 | Abbott, Jr. . |
| 3,096,283 | 7/1963 | Hein .......................................... 494/48 |
| 3,104,225 | 9/1963 | Di Benedetto . |
| 3,239,136 | 3/1966 | Hein . |
| 3,244,362 | 4/1966 | Hein . |
| 3,244,363 | 4/1966 | Hein . |
| 3,456,875 | 7/1969 | Hein . |
| 3,737,096 | 6/1973 | Jones et al. . |
| 4,142,670 | 3/1979 | Ishimaru et al. . |
| 4,303,193 | 12/1981 | Latham, Jr. . |
| 4,889,524 | 12/1989 | Fell et al. .................................. 494/60 |
| 5,316,540 | 5/1994 | McMannis et al. . |
| 5,728,040 | 3/1998 | Schill et al. . |
| 5,733,253 | 3/1998 | Headley et al. .......................... 494/47 |
| 6,007,472 | 12/1999 | Schill et al. . |

FOREIGN PATENT DOCUMENTS

| | | |
|---|---|---|
| 0 027 476 | 4/1981 | European Pat. Off. . |
| 0 654 669 | 5/1995 | European Pat. Off. . |
| 85 02560 | 6/1985 | WIPO . |

*Primary Examiner*—Charles E. Cooley
*Attorney, Agent, or Firm*—Henderson & Sturm LLP

[57] ABSTRACT

This invention proposes an improved portable and disposable centrifugal apparatus having a centrifugal processing chamber (13) of variable dimensions that can process a variable quantity of biological fluid, even down to very small quantities, by displacement of an axially movable member such as a piston (5). The invention also concerns the overall centrifugal apparatus and instrumentation cooperating with the processing chamber (13), a disposable set comprising the processing chamber (13) and a set of collection bags, as well as methods of processing biological fluids in this apparatus, in particular the collection and separation of whole blood.

24 Claims, 10 Drawing Sheets

Anticoagualant priming

Fig. 4-1

Collection

Fig. 4-2

End of collection

Fig. 4-3

Plasma extraction

Fig. 4-4

Buffy-coat extraction

Fig. 4-5

Red cell extraction

CELL SEPARATION SYSTEM WITH VARIABLE SIZE CHAMBER FOR THE PROCESSING OF BIOLOGICAL FLUIDS

FIELD OF THE INVENTION

This invention relates to the automated on line collection and separation of a biological fluid like blood into its sub-components, and relates more specifically to a functionally closed centrifugation chamber that extracts sub-components according to their density and size, such as platelets, plasma or red cells from whole blood, and to the methods for carrying out such a separation.

BACKGROUND OF THE INVENTION

Whole blood consists essentially of red blood cells, white blood cells, platelets and plasma. These components are required for different therapeutic usage and therefore whole blood resulting from a donation is generally processed in order to extract them. This is done in two steps. A first step consists in collecting whole blood from a donor into a primary bag containing an anticoagulant solution. A typical blood donation lasts between 5–10 min., to collect a fixed volume generally of 450 ml of whole blood. This fixed volume excludes a certain range of the donor population due to risks of hypovolemia, as standard blood bank practices limit collection to 15% of the total blood volume of a donor. Once the collection is completed, the donor is released and the second step can be initiated. It consists in separating the blood into its sub-components through a batch process. This is done by spinning the blood bag for a period of about 10 minutes in a large refrigerated centrifuge. The main blood constituents, erythrocytes, platelets and white cells, plasma having sedimented and formed distinct layers, are then expressed sequentially by a manual extractor in different satellite bags attached to the primary bag.

More recently, automated extractors have been introduced in order to facilitate the manipulation. Nevertheless, the whole process remains laborious and requires the separation to occur within a certain time frame to guarantee the quality of the blood components. This complicates the logistics, especially considering that most blood donations are performed in decentralized locations where no batch processing capabilities exist.

This method has been practiced since the widespread use of the disposable plastic bags for collecting blood in the 1970's and has not evolved significantly since then. Some attempts have been made to apply haemapheresis technology in whole blood donation. This technique consists of drawing and extracting on line one or more blood components while a donation is performed, and returning the remaining constituents to the donor. However, the complexity and costs of haemapheresis systems preclude their use by transfusion centers for routine whole blood collection.

There have been various proposals for portable, disposable, centrifugal apparatus usually with collapsible bags, for example as in U.S. Pat. Nos. 3,737,096, or 4,303,193, or with a rigid walled bowl as in U.S. Pat. No. 4 889,524. These devices all have a minimum fixed holding volume which requires a minimum volume usually of about 250 ml to be processed before any components can be collected.

U.S. Pat. No. 5,316,540 discloses a centrifugal processing apparatus corresponding to the precharacterizing part of claim 1, wherein the processing chamber is a flexible processing bag which can be deformed to fill it with biological fluid or empty it by means of a membrane which forms part of the drive unit.

EP-A-0 654 669 discloses a centrifugal processing apparatus having two chambers separated by a piston. Before centrifugation, a small quantity of fluid to be processed is taken in via an off-center inlet, and is transferred between the two chambers during centrifugal processing.

There remains a widespread need for a system that, during blood collection, will automatically separate the different components of whole blood that are differentiable in density and size, with a simple, low cost, disposable unit.

DISCLOSURE OF THE INVENTION

As set out in the claims, the invention therefore proposes an improved portable and disposable centrifugal apparatus whose processing chamber is of variable volume. It can therefore process a variable quantity of biological fluid, even down to very small quantities. In some embodiments, this variation of volume can be achieved with a piston which acts as a pump, providing a unique combination of a processing chamber with integrated pump.

The invention also concerns the overall centrifugal apparatus and instrumentation cooperating with the processing chamber of variable volume, as well as methods of processing biological fluids in this apparatus, in particular the collection and separation of whole blood. This new apparatus and system enable a fully automated on-line collection and separation of biological fluids even in very small quantities, opening up new perspectives in therapeutic extracorporeal processing applications. Its compactness and high portability make it ideal for mobile applications. The main components of the system are easy to manufacture from inexpensive and environmentally friendly materials, and are fully disposable. No known device meets these requirements.

The system described here allows the transfer of a biological fluid, like blood, in a functionally closed processing chamber, and its separation into sub-constituents and extraction into separate blood containers. The heart of the system is a centrifugal processing chamber which functions like a spinning syringe. Its volume is variable, preferably through a piston which can be actuated by vacuum or pressure through a port located at the bottom of the processing chamber. This provides an efficient system combining a centrifugation chamber accommodating any processing volumes, with a piston pump reducing the stressing effect on cells, unlike peristaltic pumps. No additional external pump is required for the transfer of the biological fluid or extraction of its components into or out of the processing chamber. It is however possible to use peristaltic pumps, as explained below.

Another aspect of the invention is a disposable set for collecting and separating selected quantities of biological fluids, comprising a centrifugal processing chamber as described whose inlet/outlet is connected to a means, such as phlebotomy needle, for collecting biological fluid, and to a plurality of containers, such as flexible bags, for receiving the separated components of the biological fluid. The instrumentation associated with such a disposable set is lightweight and compact. It is easily portable.

The processing chamber thus is advantageously connected, as part of a disposable set including disposable bags and tubing lines, by means of a functionally closed rotating seal. The whole set is discarded after use, to avoid the likelihood of transmission of infectious agents.

The centrifugal processing chamber has a variable volume comprised between a minimum (e.g. 0 ml) up to a maximum which corresponds to the total volume of the chamber (e.g.

500 ml). The system thus allows the separation of a minimal quantity of biological fluids starting from 10 ml upwards. As the maximum quantity that one can transfer into the processing chamber corresponds to the total volume of the chamber, this provides a self-built safety against risks of exceeding normal extracorporeal volumes.

The variation of the centrifuge chamber volume is usually performed by a piston that can move freely in the rotor of the processing chamber. The piston movement is advantageously achieved by the injection of a vacuum or air under pressure through a central port located on the bottom of the processing chamber. Such air port can be protected by a bacterial filter and is in tight communication with a centrifuge chuck assembly driving the processing chamber.

The processing chamber can have only one fluid communication port which is used both for the biological fluid transfer and the extraction of the components. Multi-port communication is also possible to provide for separate removal of different components.

The transfer of biological fluid into the processing chamber or the extraction of the sub-components does not require any external pump and can be accomplished by the downward and upward movement of a piston into the chamber. Moreover, the volume of the biological fluid processed and volumes of the sub-components extracted can be exactly metered by monitoring the position of the piston into the chamber, like a graduated syringe.

The centrifugal processing chamber is self-balanced and therefore can be driven by a compact and lightweight assembly.

The centrifugal processing chamber advantageously has an air pathway allowing movement of the piston without any physical contact of the piston with the centrifuge driving mechanism.

The above-mentioned disposable set is associated with instrumentation which allows processing and separation to take place. The instrumentation is incorporated in a lightweight and portable unit including a centrifuge spinning the processing chamber and valves for directing the components to their appropriate collection container. It is equipped with a sensor system whose information is sent to a central microprocessor unit, allowing full automation of the process.

The description relates principally to the processing and separation of whole blood but the described separation technology can apply to other types of applications like haemapheresis, blood autotransfusion, blood cell washing, or special biological cells isolation like stem cells or islets of Langerhans.

In the case of whole blood donation, this new cell separation system offers significant advantages which include:

Immediate separation of blood components is obtained during the collection. This suppresses the batch processing of blood units and facilitates the logistics of components preparation.

Component quality is improved, as immediate separation provides higher cell and protein recovery of blood components. In particular, plasma fractionation efficiency can be significantly improved if freezing of the plasma can occur immediately after the donation.

The volume of the processing chamber is variable between 0 and the total volume of the chamber (e.g. 500 ml). It can adapt to any type of donor or patient by suppressing the risks of hypovolemia. It opens up new perspectives in extracorporeal blood treatment for children, for instance.

No pumps are required, but can be used if wanted. Whole blood is drawn into the chamber through the downward movement of the internal piston and components are collected by moving the piston up again.

No risks exist of overbleeding a donor as the maximum volume that can be processed is limited by the chamber volume (e.g. 500 ml).

Volumes of blood processed and components extracted can be accurately measured by monitoring the piston position. No external scale is required.

Flexible component collection is possible by choosing one or more components and returning the other constituents to the donor.

The technology is based on conventional medical grade material and manufacturing techniques, which results in a very cost-effective system.

BRIEF DESCRIPTION OF DRAWINGS

The invention will be further described by way of example with reference to the accompanying drawings in which:

FIGS. 4-1 to 4-6 are functional diagrams showing the various steps of whole blood separation using a disposable set including a processing chamber according to the invention.

DETAILED DESCRIPTION OF THE SYSTEM

Processing Chamber

Figure 1:
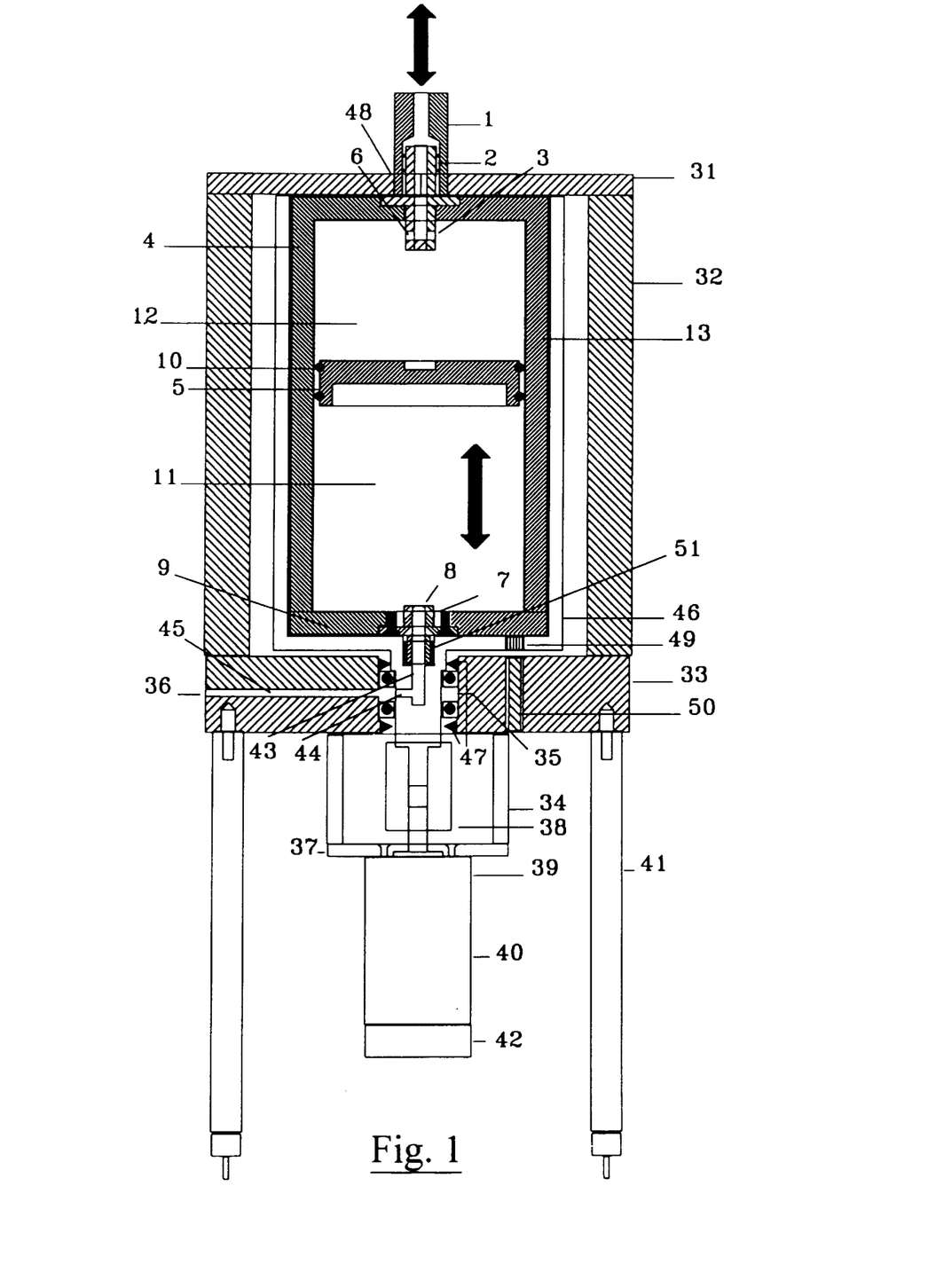
FIG. 1 is a schematic side elevation and cross-sectional view of a processing chamber according to the invention installed in a centrifugal assembly.
Figure 2:
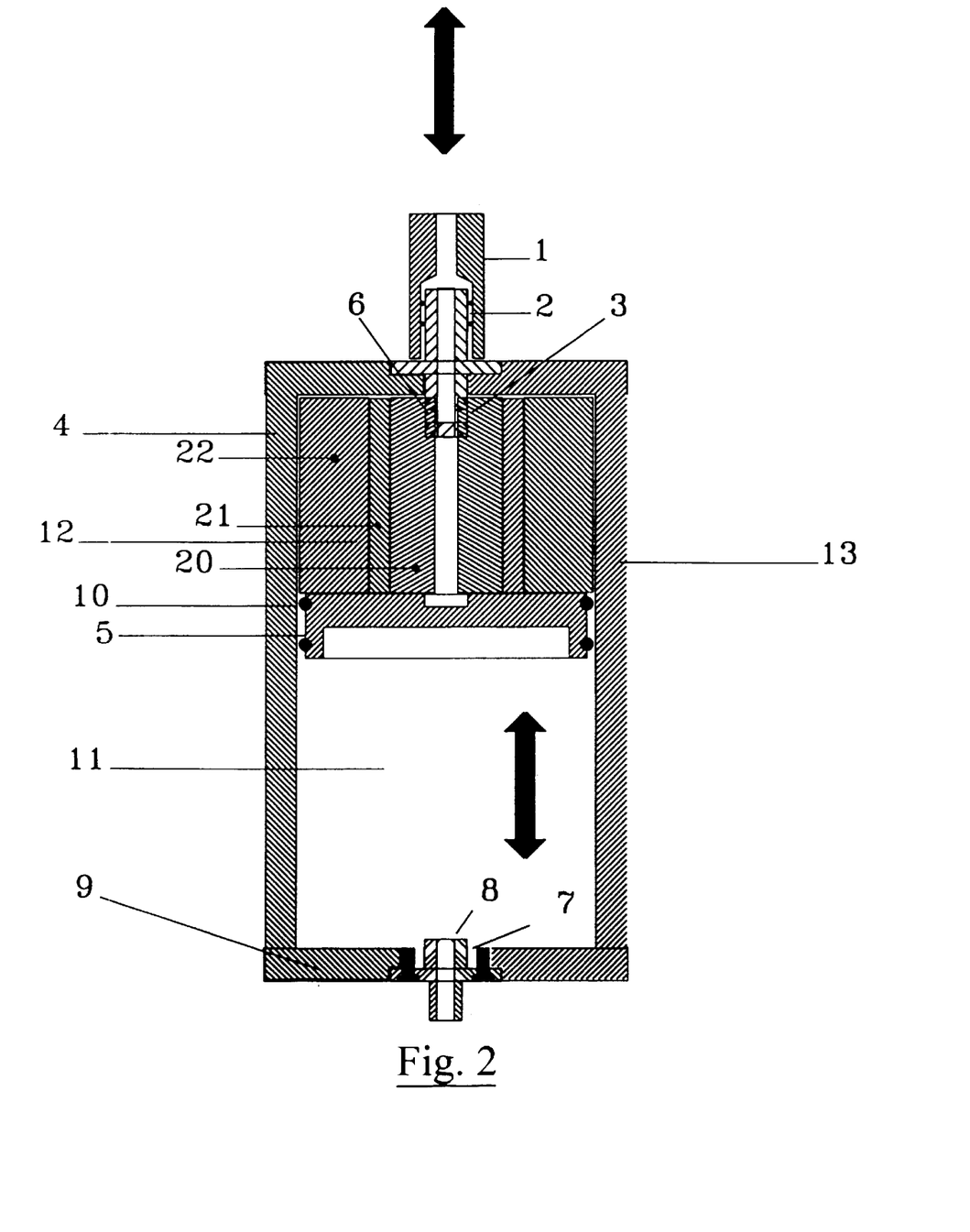
FIG. 2 is a detailed cross-sectional view of the centrifugal processing chamber illustrating the various sedimentation layers of blood components.

The processing chamber 13 in accordance with the embodiment of the invention shown in FIGS. 1 and 2 comprises a rotor 4 having a cylindrical shape, in which a piston 5 can move upwards or downwards. A variable separation space 12 is defined between the upper end of the rotor 4 and the piston 5. An inlet/outlet port 2 is located through the upper axis of the rotor 4. It is used both for the introduction of the biological fluid to separate and for the extraction of the separated components out of the chamber 13. The inlet/outlet port 2 is terminated inside the separation space 12 by a distribution disk 3 with passing holes 6 at its lower end. A rotating seal 1 is located at the other end of the inlet/outlet port 2, allowing the connection of tubing lines. Below the piston 5, the bottom cap 9 of rotor 4 has a communication port 7 for air through a central aperture equipped with a bacterial filter 8.

In this embodiment, the rotor 4 is made of a rigid injection molded plastic. A preferable material is polycarbonate or polypropylene which can withstand autoclave sterilization. The upper inlet/outlet port 2 is shown as a separate part fitted on the rotor 4, but it could be an integral part of it. The piston 5 is made of a generally cylindrical disk and is provided with peripheral grooves for O-rings 10. The tightness of these O-rings is chosen such that the piston 5 can be moved for example with vacuum/pressure values comprised in the range between –0.5/+2 bar.

This pneumatic embodiment avoids any physical contact between the piston 5 and the associated instrumentation used to drive the processing chamber 13. The bacterial filter 8 ensures that no contamination can be introduced by the air injected to move the piston. Its mesh size is generally about 0.2 microns. It should be noted that the biological fluids never come in contact with the vacuum/pressure space 11 and the bacterial filter 8 provides an additional level of system integrity.

Centrifugation generally starts when the procedure is initiated, although it can begin at a later stage when the processing chamber 13 is partially or totally filled. Initially located in the upper part of rotor 4, the piston 5 will move downward under the effect of the vacuum applied in the vacuum/pressure space 11 through the air communication port 7. The vacuum can be provided through an external air pump, connected to the central axle of the centrifuge driving the processing chamber 13.

Figure 3:
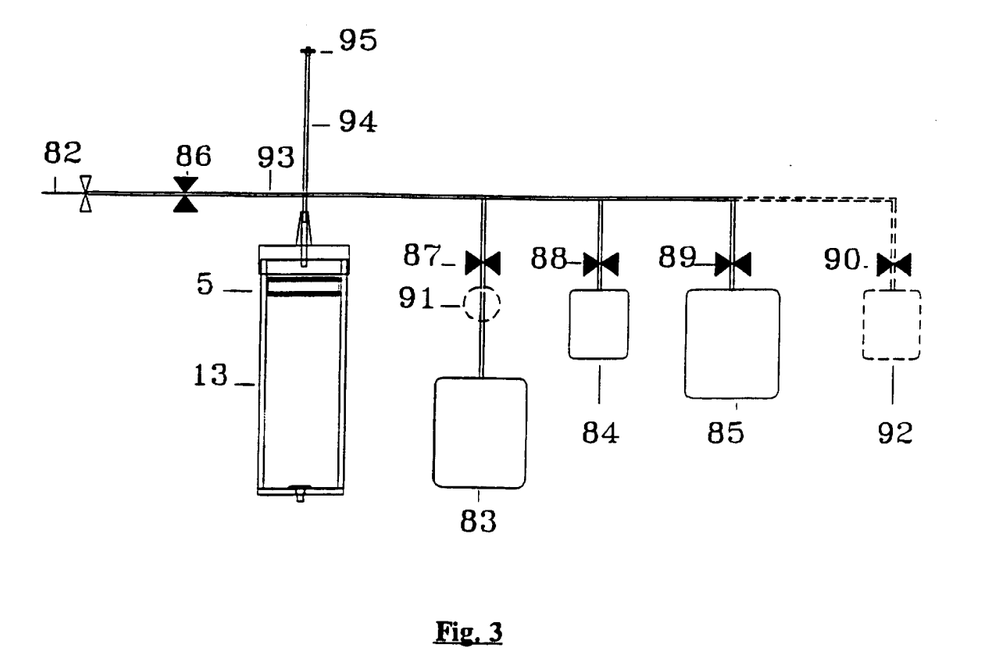
FIG. 3 illustrates in a schematic form the disposable set used for the processing and separation of blood.
Figure 7:
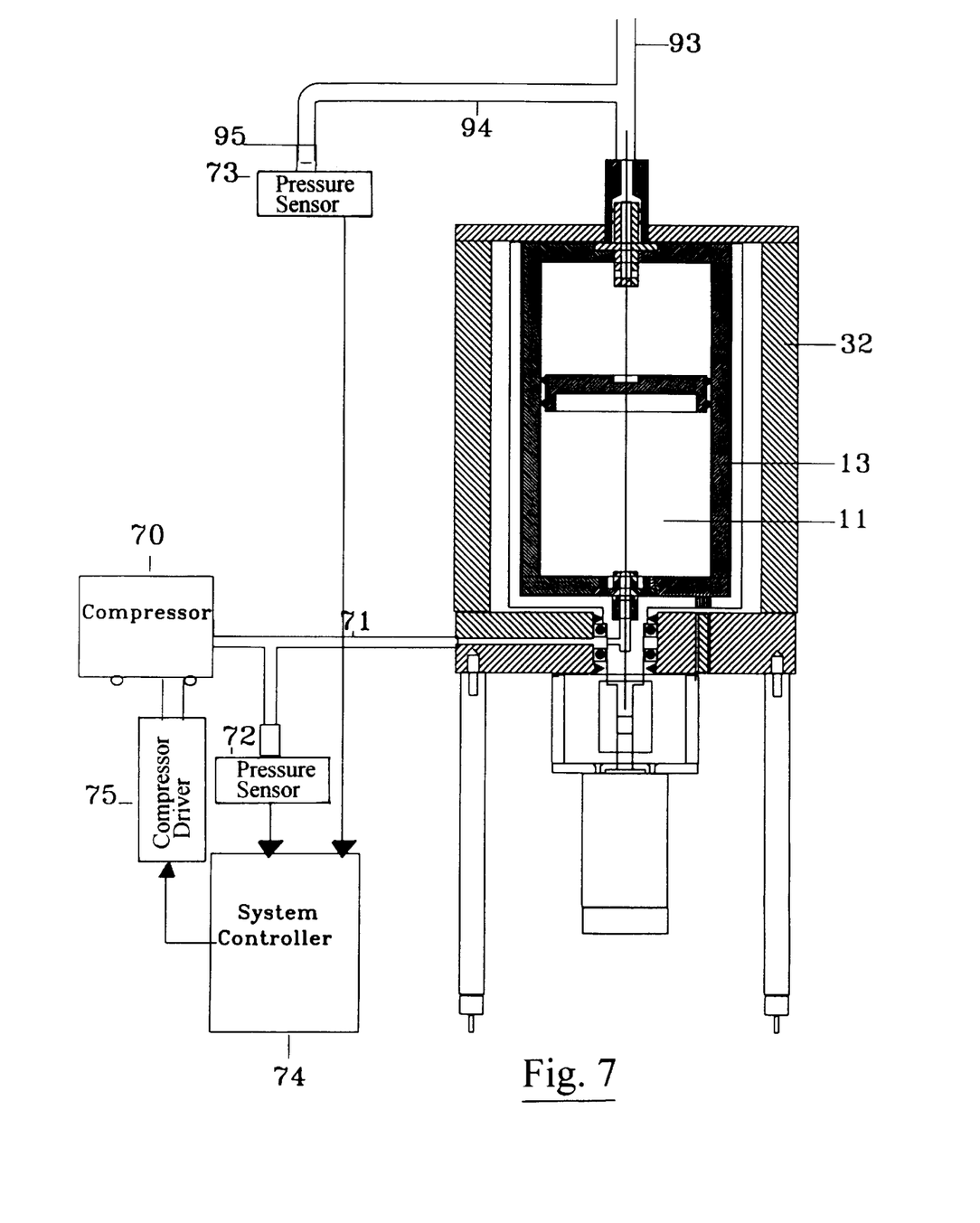
FIG. 7 schematically shows an arrangement for controlling pressure in the processing chamber when it is installed in the centrifuge assembly.

The separation space 12 is variable and is comprised between a minimum volume and a maximum corresponding to the volume of the rotor 4. Therefore, minimal quantities of biological fluids can be separated, starting from 10 ml upwards. The biological fluid passes through the rotating seal 1 and penetrates into separation space 12. Its transfer is further helped by an effect of centrifuge pumping, where the liquid introduced under rotation exercices a pressure on piston 5 that increases with the centrifuge speed. By selecting properly the rotational speed when filling, only minimal or even no vacuum is necessary to move the piston 5 down. Centrifugal separation occurs in the space 12 and the piston 5 moves slowly down in order to avoid any disturbance of the sedimentation. Its speed accommodates the donor vein capability by reading the in-line pressure measured in tubing 94 (FIG. 3) and feeding back this information to the control system. Filling rates range between 50–100 ml/min., typically. The speed is selected according to a pressure reading taken by a bacterial filter 95 which acts as a manometer (FIGS. 3 and 7). The residence time and rotational rate are selected such that heavier cellular matter is concentrated at the outer radial region.

As indicated in FIG. 2, the centrifuged biological fluid deposits in distinct layers, with lighter matter moving to the inner region of the separation space 12. Taking blood as an example, these layers are packed red cells 22 on the outside, an intermediate layer 21 of platelets/white cells generally called buffy-coat, and plasma 20 inside.

When the piston 5 reaches the bottom of the rotor 4 (or upon decision of the operator), an additional sedimentation period can be initiated at higher centrifugation speed to accelerate the component separation. The movement of piston 5 can then be inverted by applying a pressure into the vacuum/pressure space 11 through the air communication port 7. The piston 5 moves slowly up again with a speed avoiding any interference with the sedimentation of the components. Lighter matter exits first and will pass through the upper inlet/outlet port 2. Components of increasing density and size will sequentially follow. Heavier matter will finally be expressed and the collection ends when the piston 5 reaches the upper end of the rotor 4. It should be noted that centrifugation can be stopped before the last component is extracted to facilitate its extraction. At that time another processing cycle can resume if desired.

The volume of biological fluid introduced into the processing chamber 13 or the volumes of the extracted components can be exactly measured by monitoring the position of the piston 5 during the process, like a graduated syringe.

Application for Whole Blood Separation

FIG. 3 illustrates an application for whole blood separation. It will be understood however that this is only one example of application of the cell separator and method of the present invention, and other specific applications can be carried out utilizing the invention system.

The disposable set used for this separation comprises a centrifugal processing chamber 13 (like the processing chamber of FIGS. 1 and 2) connected to a set of tubing lines and bags. A schematically-indicated phlebotomy needle 82 is connected to a tubing line 93 which connects the processing chamber 13 to a plasma bag 85, a buffy-coat bag 84 and a red cell concentrate bag 83. A portion of so-called pigtail tubing 94 terminated with a bacterial filter 95 is connected to the inlet tubing of the processing chamber 13 for pressure measurement (see also FIG. 7).

Anticoagulant like CPD (Citrate-Phosphate-Dextrose) can be contained initially in the plasma bag 83, for transfer into the processing chamber 13 when the procedure is initiated. This is only one way the anticoagulant can be transferred. Alternatives would be to have the processing chamber 13 pre-filled with anticoagulant, or to have an additional bag containing only the anticoagulant. The red cell bag 83 may contain an additive solution to extend the shelf life of erythrocytes.

An optional additional bag 92 contains a special substance for further transfer into the appropriate blood component bags in order to inactivate virus. Another possibility of the system consists in filtering on line components for leukocytes removal, using optional filter 91 for the collection of leukocyte-free red cells. Valves 86–90 are associated with the tubing line 93, as illustrated in FIG. 3, namely donor line valve 86, red cell line valve 87, buffy-coat line valve 88, plasma line valve 89 and spare valve 90. These valves are located on the instrument as indicated by reference 102 on FIG. 5, and serve to open/close the tubing lines according to the procedure step.

It should be noted that the bags 83,84,85,92 are not exposed to a stress-causing G force as presently with the batch centrifugation process. The options for design and material choice of the bags are therefore extensive. This facilitates the compliance to regulatory standards for having an environmental friendly disposable material.

Figure 41:
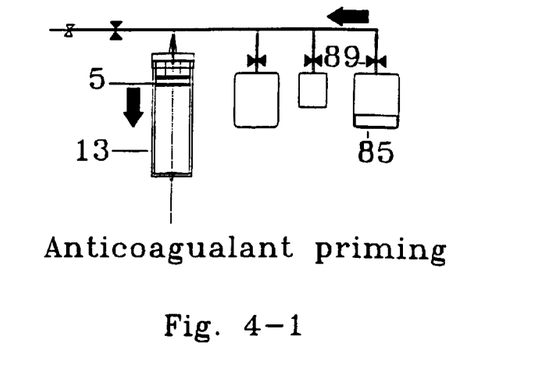

The separation of whole blood is sequential and components of increasing density and size are collected. Separation takes place in six steps illustrated in FIGS. 4-1 to 4-6. Centrifugation can start at any time from step 1, 2 or 3. The separation steps are:

Step 1: Anticoagulant priming of the processing chamber 13 by moving the piston 5 downwards. Valve 89 is open and anticoagulant is pumped out of plasma bag 85. This step can be avoided if the processing chamber is pre-filled with the anticoagulant solution.

Figure 42:
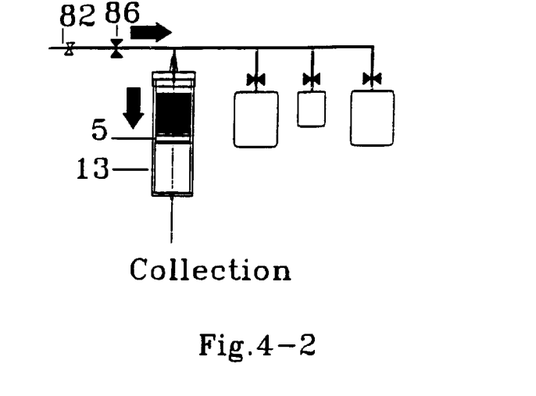

Step 2: Whole blood collection, by moving the piston 5 downwards and opening valve 86.

Figure 43:
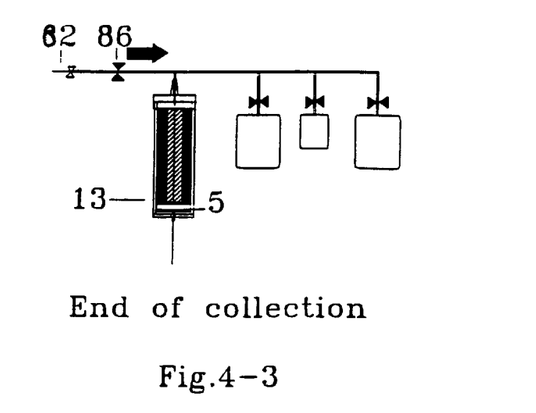

Step 3: The piston 5 reaches the bottom of the processing chamber 13, or when stopped by the operator or at a pre-set value. Collection stops. The phlebotomy needle 82 can be disconnected.

Figure 44:
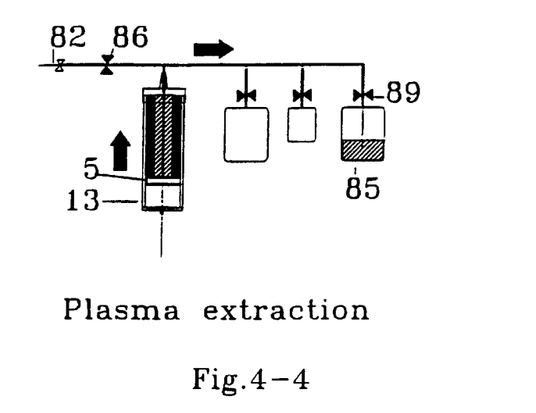

Step 4: Extraction of plasma, by moving the piston 5 upwards. Donor valve 86 is closed, plasma valve 89 is open. Plasma is collected into bag 85.

Figure 45:
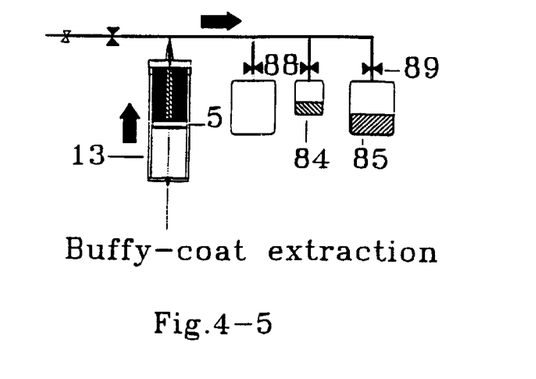

Step 5: Buffy-coat extraction, by moving slowly the piston 5 upwards. Plasma valve 89 is closed and 12 buffy-coat valve 88 is open. Buffy-coat is collected into bag 84.

Figure 46:
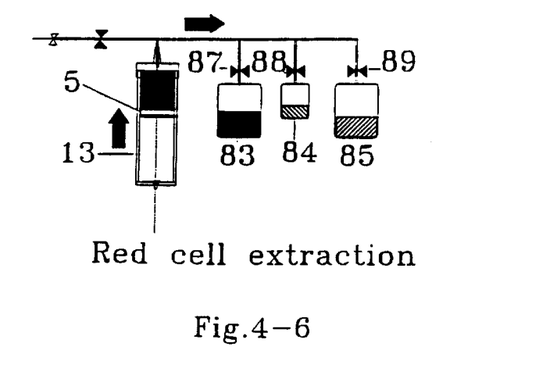

Step 6: Red cell extraction, by moving the piston 5 upwards. Centrifugation is stopped, although it can be continued if differential separation of red cell collection is desired. Buffy-coat valve 88 is closed and red cell valve 87 is open. Packed red cells are collected into bag 83. Extraction of red cells is completed when the piston reaches the top of the processing chamber 13.

Centrifuge Assembly/Instrumentation

Figure 6:
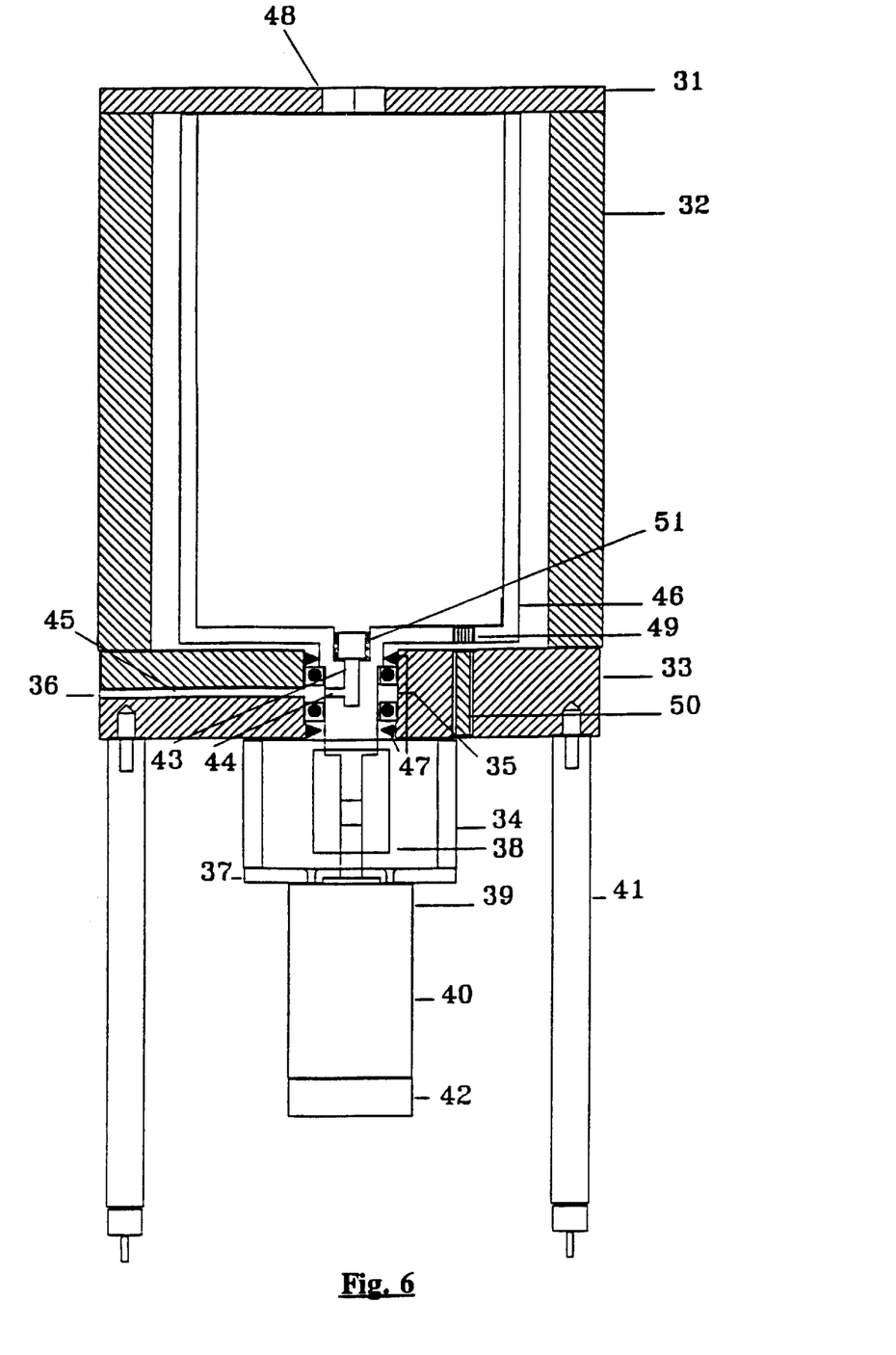
FIG. 6 is a schematic side elevation and cross-sectional view of a centrifugal assembly.

The centrifuge drive unit is illustrated in FIG. 1 with the processing chamber fitted, in FIG. 6 without the processing chamber, and in FIG. 7 with the associated arrangement for controlling pressure. It should be noted that although shown vertically it can be operated in any position.

Referring to FIG. 1, a chuck 46 of generally cylindrical shape with a longitudinal hollow axle 43 underneath is used to drive the centrifuge processing chamber 13. Axle 43 coincides with the centrifuge axis. The chuck 46 has an O-ring 51 mounted in an aperture in its bottom. The O-ring 51 frictionally engages the lower outer portion of the air communication port 7 of the inserted processing chamber 13, providing fluid-tight communication with a vacuum/pressure port 36 through which vaccum or air under pressure is supplied from an external source (see FIG. 7). A bearing assembly 35 ensures proper alignment of the chuck 46. Seam rings 47 are located on each side of the bearing assembly 35. Between the two bearings of bearing assembly 35, the axle 43 has a vacuum-pressure passing hole 44 that communicates with the vacuum/pressure port 36, through a pneumatic path 45.

The chuck 46 is housed within a stationary cylindrical housing 32, which is mounted on a support plate 33. The housing 32 carries a closing cover 31 on its top, along with an associated rotating seal holder 48. The cover 31 is composed of two symmetric planar and semi-circular half-discs, that can be moved apart and together so the rotating seal holder 48 can grip the rotating seal 1.

A proximity sensor 50 is secured in the support plate 33 and measures the displacement of the piston 5 for volume and flow rate control. For example, this sensor 50 passes an optical beam through an aperture 49 in the chuck bottom, and which is reflected back by the piston 5. Alternatively, for monitoring the piston displacement, infrared Doppler sensors, inductive or Hall effect sensors could be used.

The pressure/vacuum value in the space 11 is constantly measured by a pressure sensor 72 connected to line 71 (FIG. 7) during operation. The pressure in tubing line 94 is also measured by an in-line pressure sensor 73. This information is fed-back to a control system 74 controlling a compressor driver 75. An algorithm adjusts the power of compressor 70 according to the values of these pressure readings.

The centrifuge is mounted in a cabinet (see FIG. 5) on three cylindrical centrifuge support feet 41. An electrical motor 39 enclosed in a housing 40 with a tachometer 42 fitted on its lower end is attached through a coupling 38 to the chuck axle 43. The rotation speed ranges between about 3000–10000 rpm depending on the application. Motor 39 is mounted on a shaft support plate 37 which is attached to the support plate 33 by shaft housing 34. The processing chamber 13 being self-balanced, the whole centrifuge assembly herein described can be made very light and compact.

Figure 5:
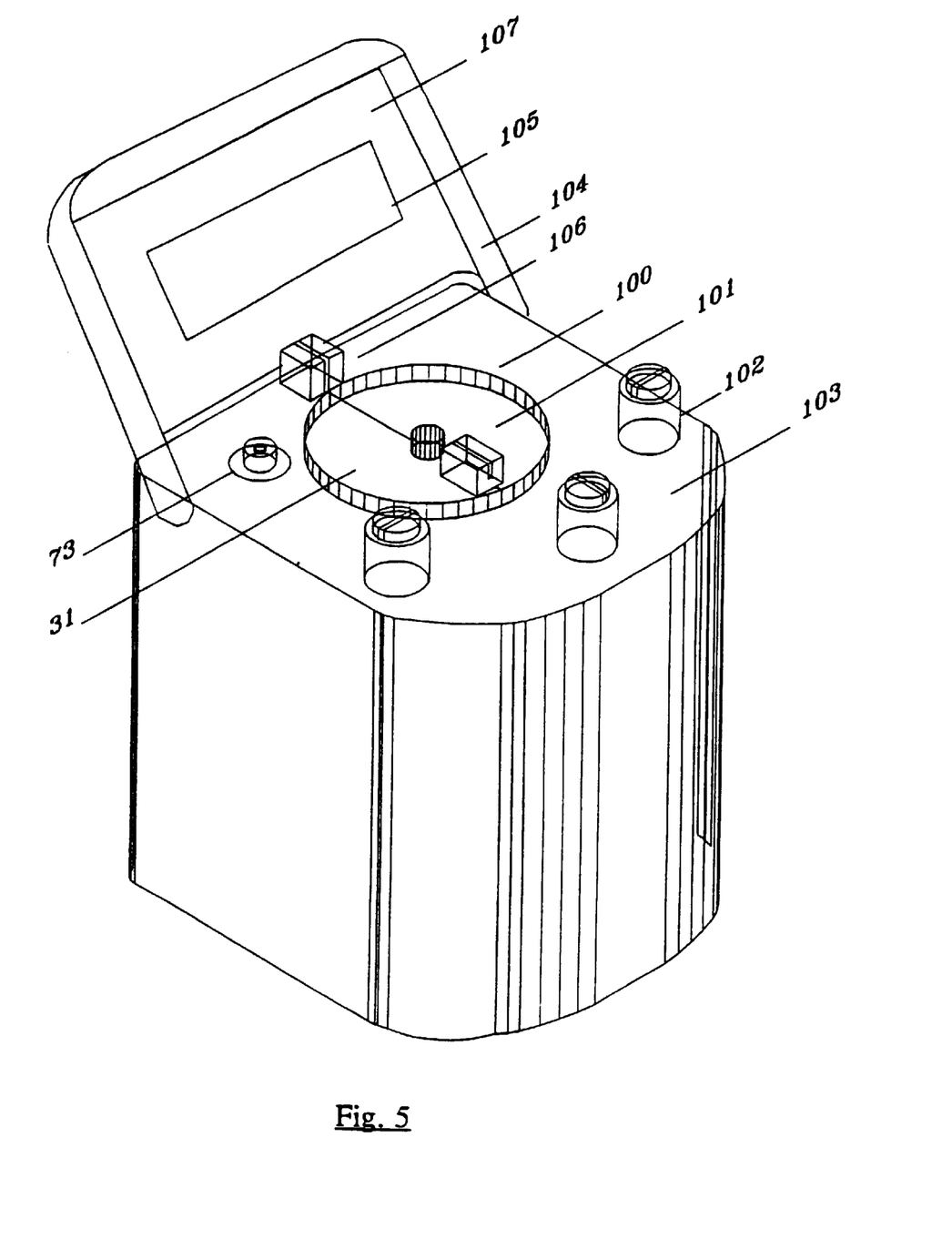
FIG. 5 is a perspective view of a cabinet containing instrumentation for controlling the processing.

As illustrated in FIG. 5, the instrumentation is composed of a cabinet 103 housing a centrifuge 100. It is lightweight and compact which makes this device especially useful for portable applications. The cabinet 103 is made of a reinforced material like ABS. The centrifuge 100 drives the processing chamber 13 at speeds up to 10000 rpm. Valves 102 (i.e. corresponding to 86–90 of FIG. 3) equipped with position sensors are located on the top of the cabinet housing. These valves clamp the proper tubing lines (FIG. 3) for collecting the separated products. Sensors are provided to monitor the pressure inside the processing chamber 13 and piston chambers. An optical sensor 101 controls the appropriate collection of blood constituents like plasma, platelets or red cells and commutes the valves 102 according to the desired separation steps illustrated in FIG. 4-1 to FIG. 6. An ultrasonic air detector 106 monitors the presence of air in the donor line. The cover 104 provides access to the operator-controlled instrumentation. When the cover 104 is open, it is inclined at a 20° angle for ease of viewing. The cover 104 has a panel 107 mounted on the inside with a display and control functions module 105 incorporated therein.

VARIATIONS

Figure 8:
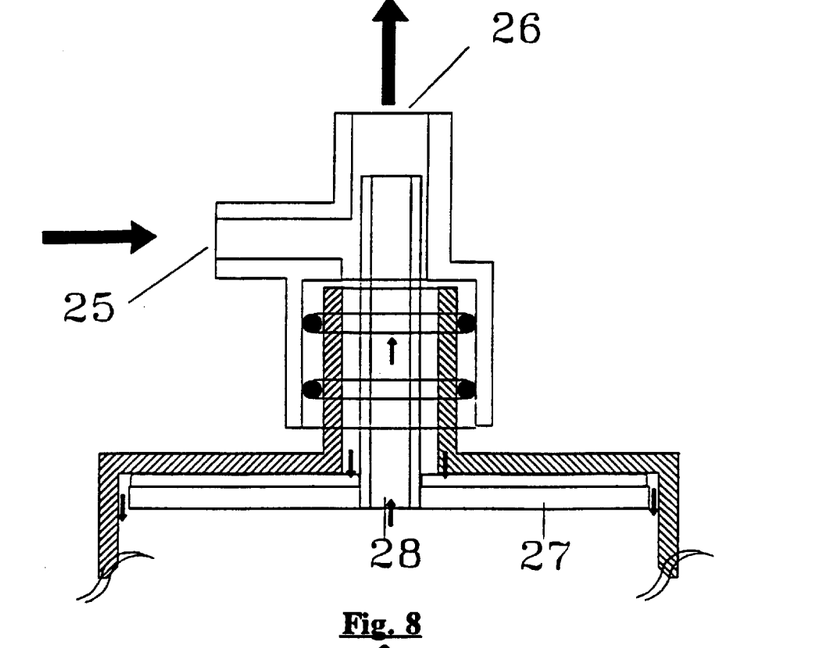
FIG. 8 is a schematic side elevation and cross-sectional view of the upper part of a dual port processing chamber.

The previously-described system uses a single port for transferring fluids in and out of the processing chamber. FIG. 8 shows a dual port configuration allowing a continuous operation, where collection of the desired component can take place while the product to be separated is introduced into the processing chamber. As shown, an inlet port 25 leads onto a distribution or spreader disk 27 located at the upper end of chamber 13, so that incoming biological fluid is directed, as indicated by the arrows, to the disk's periphery where the fluid is ejected with the maximum centrifugal force against the chamber wall. An outlet port 26 is located in extension of a central outlet tube 28 leading into the separation space through the center of the distribution disk 27. Consequently, the separated components exit centrally via this tube 28 and outlet port 26, also as indicated by arrows.

In the case of this dual port configuration, continuous operation can be performed using one external pump like the peristaltic pump 110 (FIG. 10) for transferring the biological fluid into chamber 13 via port 25 and distribution desk 27. The piston 5 moves in response to the volume of fluid introduced until the bottom of the chamber is reached, or until stopped at an intermediate position. Two methods can be chosen for extracting the components out of the chamber 13 via tube 28 and port 26. The first consists in continuing filling the chamber so the packed red cells will gradually push the other components out of the chamber 13. The other consists of stopping the peristaltic pump 110, moving the piston 5 up, and the collection of components will be done as illustrated in steps 4-4 to 4-6 of FIG. 4. A multiport system could also be used, where more than one component could be collected out of the chamber simultaneously.

In the described example, the piston 5 is driven by vacuum/compressed air. It would equally be possible to drive the piston by mechanical, electromagnetic or hydraulic means, possibly under electronic control. In the case of hydraulic means, the piston 5 can be moved by sterile fluid that can be pumped in and out of the space 11 of the processing chamber 13.

An alternative would be to have the piston 5 replaced by a flexible and collapsible membrane attached to the upper part of the rotor 4, which can be extended or retracted by application of a vacuum/pressure or by hydraulic action.

In another variation, the rotor 4 of processing chamber 13 can be made of a flexible material like a soft bag which, during rotation, would be supported by the centrifuge chuck 46 so as to maintain a cylindrical shape.

Figure 9:
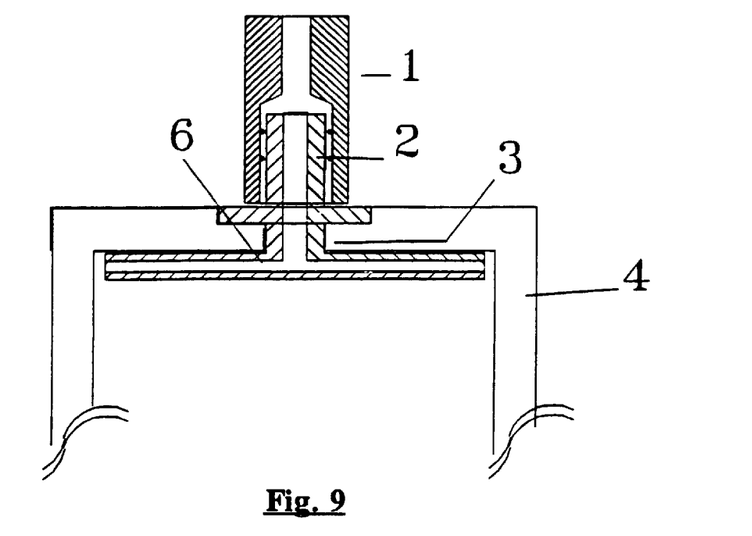
FIG. 9 is a schematic side elevation and cross-sectional view of an extended distribution disk allowing heavier matter to exit the processing chamber first.

Another variation shown in FIG. 9 consists of having the distribution disk 3 of a diameter close to the internal diameter of rotor 4. When the separated components are expressed out of chamber 13, this would allow the higher density cells like red cells to be sorted first, which would be of interest in red cell autotransfusion for example.

Figure 10:
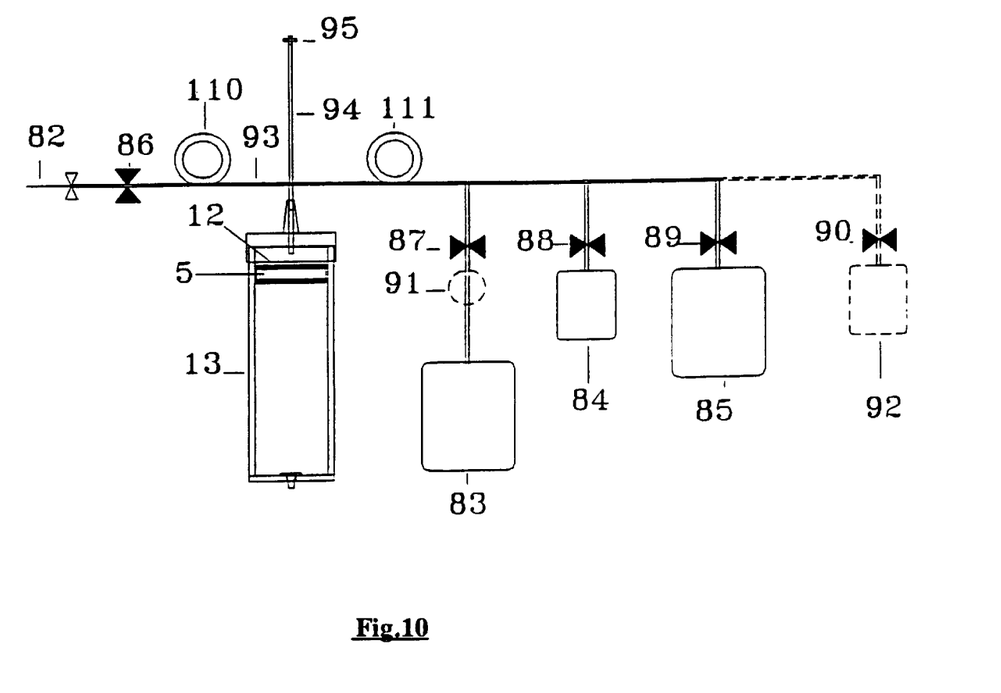
FIG. 10 illustrates in schematic form a system using peristaltic pumps as a means to introduce and extract biological fluids into and out of the processing chamber.

Another variation shown in FIG. 10 consists of transferring fluids in and out of the processing chamber 13 by means of peristaltic pumps 110 and 111 acting on the tubing line 93, respectively to deliver blood into the processing chamber 13 and to remove the separated components from the processing chamber 13. In this case, the piston 5 does not act as a pump, but only as a means to vary the volume of the separation space 12. Consequently it is no longer necessary to use pneumatic means, or any other equivalent means, to move the piston 5. The use of peristaltic pumps is recommended for carrying out haemapheresis procedures, in particular using the dual port arrangement of FIG. 8.

Another variation consists of having the upper part of the rotor 4, as well as the upper part of the piston 5, of a conical shape in order to allow a smoother fluid path out of the processing chamber.

OTHER APPLICATIONS

The apparatus of the present invention is particularly suited for the separation and collection of blood components. As described above, a main application is in-line whole blood separation. Other applications include:

1) Hemapheresis

It is possible to use the system in an haemapheresis mode where one or more components are returned to the donor or patient. In this case, the instrumentation should incorporate the necessary components and modules to manage the reinfusion procedure. Proper anticoagulation should also be provided at the needle site, with proportional mixing to ensure that no clot formation will occur in the line.

2) Autotransfusion

Figure 11:
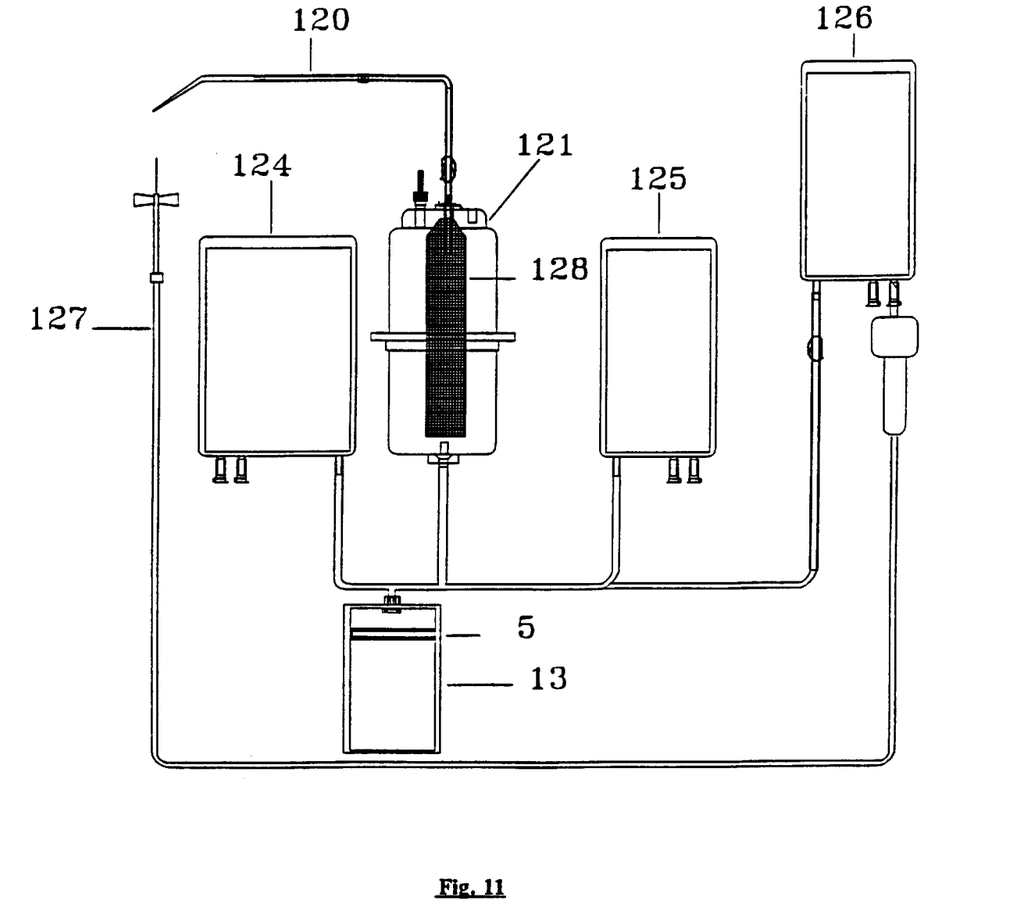
FIG. 11 illustrates in schematic form a system for intraoperative blood autotransfusion based on the processing chamber with variable volume.

Blood autotransfusion, and more generally cell washing can also be performed with the present invention, as shown in FIG. 11. In the case of intraoperative autotransfusion, shed blood would be aspirated through a suction line 120 into an autotransfusion reservoir 121 containing a mesh or depth filter 128. The filtered blood could then be transferred into the processing chamber 13 by moving down the piston 5. Supernatant would be expressed out of the chamber 13 in a waste bag 124 and centrifugation would then be stopped. A washing solution contained in bag 125 would be introduced into the processing chamber 13 and centrifugation would resume upon filling of the chamber. Supernatant would be expressed again in bag 124, and another washing step could resume at this stage. Washed red cells would then be recovered in bag 126 by moving up piston 5. Gravity reinfusion would then be initiated to the patient through reinfusion line 127.

The efficiency of this blood autotransfusion system could be advantageously improved by using a dual port configuration chamber as shown in FIG. 8 and a peristaltic pump 110 as shown in FIG. 10.

Post-operative blood autotransfusion would also be possible using the processing chamber 13 in a static mode where only the piston 5 would be moved for establishing the drainage vacuum. Upon filling the processing chamber 13 or completion of the drainage period, centrifugation of the processing chamber 13 would be started and shortly afterwards the piston 5 lifted in order to express the supernatant. Red cells could then be recovered or washed as described above for intraoperative autotransfusion.

3) Cell Isolation

In certain therapeutic applications it is desirable to concentrate specific types of cells such as stem cells, that are present either in the blood or in the bone marrow. In this latter case, the system will function in a batch process and the cells, contained in their physiological medium, would be introduced by moving the piston down. The targeted cells will be expressed out of the processing chamber 13 into the appropriate collection bag. The process is repeated until the initial product has been processed, at which time an ultimate cell purification process can be done by reintroducing the collected cells into the chamber for a final concentration and expressing them into the collection bag.

4) Other Physiological Liquids

In addition to blood, the system can be used for the separation of other physiological fluids such as medium containing islets of Langerhans, or certain type of tumoral cells for further biotechnological manipulations.

What is claimed is:

1. A centrifuge apparatus for processing biological fluids, comprising a hollow centrifuge processing chamber rotatable about an axis of rotation by engagement of the processing chamber with a rotary drive unit, the processing chamber having an axial inlet/outlet with an inlet and an outlet for biological fluid to be processed and for processed components of the biological fluid, said inlet/outlet leading into a separation space of variable volume wherein the entire centrifugal processing of biological fluid takes place, said processing chamber comprising a generally cylindrical wall extending from an end wall of the processing chamber, said generally cylindrical wall defining therein the hollow processing chamber which occupies a hollow open cylindrical space coaxial with the axis of rotation, the axial inlet/outlet being provided in said end wall coaxial with the generally cylindrical wall to open into the hollow processing chamber, the processing chamber containing within said generally cylindrical wall an axially moveable member, said separation space of variable volume being defined in an upper part of the processing chamber by said generally cylindrical wall and by said axially moveable member contained in the generally cylindrical wall of the processing chamber, wherein axial movement of said moveable member varies a volume of the separation space, the moveable member being axially moveable within the processing chamber to intake a selected quantity of biological fluid to be processed into the separation space via said inlet at a time selected from before and during centrifugal processing and to express processed biological fluid components from the separation space via said outlet during or after centrifugal processing.

2. The apparatus of claim 1, wherein the movable member comprises a piston fluid-tightly movably mounted in the processing chamber.

3. The apparatus of claim 2, comprising a member selected from the group consisting of pneumatic means, hydraulic means, mechanical means and electromagnetic means as means for driving the piston whereby the piston acts as a pump.

4. The apparatus of claim 3, wherein said means for driving the piston is located externally of the processing chamber, there being no physical contact between said means for driving and the piston.

5. The apparatus of claim 4, wherein said means for driving acts on the piston via a medium selected from the group consisting of sterile pneumatic medium and hydraulic medium.

6. The apparatus of claim 5, wherein the processing chamber comprises an axial opening equipped with a bacterial filter adapted for fluid-tight connection of the processing chamber to a source of the medium.

7. The apparatus of claim 2, comprising means for monitoring a position of the piston to control an amount of intaken biological fluid and expression of separated components.

8. The apparatus of claim 1, wherein the processing chamber comprises a single inlet/outlet opening for both intake of the biological fluid to be separated and removal of separated components.

9. The apparatus of claim 1, wherein the processing chamber comprises an inlet/outlet comprising one port for intake of the biological fluid to be separated and at least one separate port for removal of separated components.

10. The apparatus of claim 9, wherein said port for intake of biological fluid cooperates with a distribution disk directing incoming fluid to a periphery of said disk where the biological fluid is exposed to maximum centrifugal force.

11. The apparatus of claim 1, wherein said axial inlet/outlet comprises a rotatable seal mountable in a stationary housing.

12. The apparatus of claim 1, further comprising a drive unit for the processing chamber, said rotary drive unit comprising a rotary chuck for receiving the processing chamber, said chuck being rotatably mounted inside a stationary housing and connected via a path selected from a group consisting of a pneumatic path and a hydraulic path to an external source of medium selected from the group consisting of pneumatic medium and hydraulic medium, the stationary housing having a cover with an aperture receiving means for rotatably mounting the inlet/outlet of the processing chamber.

13. A disposable set for collecting and separating selected quantities of biological fluids comprising the centrifugal processing chamber of an apparatus according to claim 1, wherein the inlet/outlet of the processing chamber is connected to a means for collecting biological fluid and to a plurality of containers for receiving separated components of the biological fluid.

14. The disposable set according to claim 13, wherein the means for collecting biological fluid is associated with a collection valve for controlling intake of biological fluid from said means for collecting biological fluid into the processing chamber and each of said containers is associated with a container valve for controlling delivery of expressed separated components of the biological fluid into respective containers.

15. A centrifuge apparatus for processing biological fluids in combination with a disposable set as claimed in claim 14, wherein the apparatus further comprises means for selectively actuating the collection valve and the container valves to control intake of biological fluid into the processing chamber and delivery of expressed separated components of the biological fluid into the respective containers.

16. The disposable set according to claim 13, further comprising at least one filter for on-line filtering of separated components.

17. A method of processing biological fluids in an apparatus according to claim 1, comprising intaking a selected variable quantity of biological fluid into the separation space with corresponding movement of the movable member within the processing chamber, centrifuging the biological fluid in the separation space for a time selected from the group consisting of during, after, and during and after intaking the biological fluid, and moving the member back to express centrifuged fluid components via said outlet of said axial inlet/outlet.

18. The method of claim 17, wherein the movable member comprises a piston, and wherein movement of the piston is controlled by means selected from the group consisting of pneumatic means, hydraulic means, mechanical means and electromagnetic means to select a volume of biological fluid intaken into the separation space and to selectively express separated components.

19. The method of claim 18, wherein movement of the piston to intake biological fluid is assisted by a centrifugal pumping effect produced by pressure exerted on the piston by incoming biological fluid.

20. The method of claim 17, wherein the intaken fluid is drawn from a blood autotransfusion reservoir; supernatant and washed solutions are expressed in a waste container; and red cells are expressed in a collection container; all by moving the movable member.

21. The method of claim 18, comprising monitoring a position of the piston to intake a selected variable quantity of biological fluid and to selectively express separated components.

22. A method comprising using the apparatus of claim 1 for processing variable volumes of biological fluid from 10 ml up to a maximum volume of the separation space.

23. A method according to claim 22, wherein said biological fluid comprises whole blood and said processing comprises whole blood collection and separation.

24. A method according to claim 22, wherein said biological fluid comprises shed blood and said processing comprises shed blood washing and recovery.

* * * * *